(12) United States Patent
Dickholtz, Sr. et al.

(10) Patent No.: US 7,131,952 B1
(45) Date of Patent: Nov. 7, 2006

(54) METHOD AND APPARATUS FOR MEASURING SPINAL DISTORTIONS

(76) Inventors: Marshall Dickholtz, Sr., 7521 N. Keystone Ave., Lincolnwood, IL (US) 60046; Mary Ann Dickholtz, 7521 N. Keystone Ave., Lincolnwood, IL (US) 60046

( * ) Notice: Subject to any disclaimer, the term of this patent is extended or adjusted under 35 U.S.C. 154(b) by 215 days.

(21) Appl. No.: 10/893,481

(22) Filed: Jul. 15, 2004

(51) Int. Cl.
  *A61B 5/103* (2006.01)
  *A61B 5/117* (2006.01)
  *A61B 1/00* (2006.01)
  *G01B 1/00* (2006.01)

(52) U.S. Cl. .......................... 600/594; 600/587; 33/512

(58) Field of Classification Search ............... 600/587, 600/594, 595; 33/512, 1 C, 1 G, 1 K, 1 BB, 33/286, DIG. 21
See application file for complete search history.

(56) References Cited

U.S. PATENT DOCUMENTS

| | | | |
|---|---|---|---|
| 379,206 A * | 3/1888 | Brackett | 33/476 |
| 3,363,504 A * | 1/1968 | Lill | 359/855 |
| 3,699,856 A | 10/1972 | Chabot et al. | |
| 4,135,498 A | 1/1979 | McGee | |
| 4,425,713 A | 1/1984 | Rotella | |
| 4,600,012 A | 7/1986 | Kohayakawa et al. | |
| 4,662,079 A * | 5/1987 | Graf et al. | 33/512 |
| 5,088,504 A | 2/1992 | Benesh et al. | |
| 5,203,346 A | 4/1993 | Fuhr et al. | |
| 5,398,697 A * | 3/1995 | Spielman | 600/594 |
| 5,443,079 A | 8/1995 | Greenawalt | |
| 5,954,674 A | 9/1999 | Fuhr | |
| 5,966,827 A | 10/1999 | Horvath et al. | |
| 6,159,168 A | 12/2000 | Warner et al. | |
| 6,206,787 B1 * | 3/2001 | Kleppen | 473/207 |
| 6,263,584 B1 * | 7/2001 | Owens | 33/640 |
| 6,468,233 B1 | 10/2002 | Cook | |
| 6,514,219 B1 | 2/2003 | Guimond et al. | |
| 6,565,519 B1 | 5/2003 | Benesh | |

OTHER PUBLICATIONS

Bozic, B. et al. Biomechanical Analysis of the Lumbar Spine. Minim. Invas. Neurosurg. 40(1997) 24-26.*

* cited by examiner

*Primary Examiner*—Max F. Hindenburg
*Assistant Examiner*—Michael Apanius
(74) *Attorney, Agent, or Firm*—Lloyd L. Zickert

(57) ABSTRACT

A method and apparatus for measuring the spinal distortions of a person with laser sources prior to and after chiropractic treatment of a patient to differentiate between spinal distortions prior to and subsequent to any treatment. The apparatus includes a wall chart having measurement indicia, shoulder and/or pelvic girdle harnesses or frames mounted on a patient and each having means for projecting laser line and/or dot beams onto the wall chart for measuring spinal tilt and torque. A unique protractor is provided to coact with the wall chart and the laser line beam to measure spinal tilt. A laser source for projecting a vertical line beam measures abnormalities in posture by projecting the beam to a side of a patient.

34 Claims, 9 Drawing Sheets

METHOD AND APPARATUS FOR MEASURING SPINAL DISTORTIONS

This invention relates in general to a method and apparatus for measuring the spinal distortions of a patient before and after chiropractic treatment of the patient, and, more particularly, to a method and apparatus that includes the use of laser sources to define laser line and/or dot beams and a wall chart for measurement of spinal tilt and/or torque.

BACKGROUND OF THE INVENTION

The orthodox purpose of chiropractically treating a patient includes the correction, and/or restoration toward normal of any misalignments of subluxated vertebrae by adjusting any subluxated vertebrae to their normal relative position. A subluxation of vertebrae is a condition caused by vertebral misalignments resulting from the abnormal movement of subluxated vertebrae that, through pressure, interference of an irritation, and/or disruption of spinal sensors, produces detrimental effects on the nervous system. These misalignments affect the spinal column and the vertebral canal and can cause abnormal functioning of the central nervous system. As such, these spinal misalignments may manifest themselves in a variety of conditions or diseases for a person.

The atlas vertebra, also known as "C-1" vertebra, is the most important vertebra in the spinal column because it is the uppermost vertebra of the human spine, and is not fixed or locked in place by boney articulations. It also supports the skull in close proximity to the caudal region of the brain stem.

It has been known that spinal distortion is accompanied by and correlates with some misalignment in the atlas vertebra in one or more planes of its positionable relationship to the patient's head and spine. Accordingly, it is desirable to quickly and accurately measure the misalignments along the spinal column and body.

In order to determine the correction of subluxations, it is important to have precise X-rays as the primary source of information as to the location of the atlas vertebra and adjacent vertebrae. Heretofore, it has been normal routine to take a series of X-rays in three planes of motion in which the spinal vertebrae can abnormally move to determine misalignment. After the adjustment or procedure, a second series of X-rays would be taken to conduct an appraisal of the spine to determine the degree of correction of the misalignments.

Heretofore, it has also been well known to measure the accomplished correction of subluxations by use of a machine called an anatometer in order to reduce the need for some X-rays. Such an anatometer is disclosed in U.S. Pat. No. 5,088,504. Such a machine is very costly, and therefore, not affordable in every chiropractic office. It does not measure the shoulder girdle position and provide a true pelvic torque or torque to the whole spine. Accordingly, there is a need to provide a method and apparatus for measuring spinal distortions before and after chiropractic treatment which is easy to use and will provide accurate measurements of spinal distortion at a nominal cost, and which will provide knowledge for better detection of a subluxation and distortion of the spine. This will also reduce the need for some X-rays.

SUMMARY OF THE INVENTION

The present invention more accurately and inexpensively overcomes the problems of measuring spinal distortions and reduces the use of some X-rays. This method and apparatus includes the use of a wall chart having measurement indicia to measure spinal tilt and torque, and means for mounting laser sources on the shoulder and/or pelvic girdles or areas of a patient facing the wall chart for projecting laser line and/or dot beams onto the chart to measure the spinal tilt and torque at a patient's shoulder and/or pelvic areas. It will be appreciated that "spinal tilt" constitutes a deviation or distortion of the spine to the right or left of the substantially vertical axis or the sagittal plane of a person, while "spinal torque" constitutes a deviation or distortion of the spine clockwise or counterclockwise about a substantially vertical axis or transverse plane of a person.

Preferably, the apparatus of the invention includes a wall chart, a shoulder girdle harness or fixture mountable on the shoulders of a patient and a pelvic girdle harness or fixture mounted on the pelvic area of a patient. Each of the harnesses includes one or more laser sources for projecting laser line and/or dot beams onto the chart to measure the spinal tilt and torque at the shoulder and pelvic areas of a patient. The projection of a line beam which is substantially horizontal, and aligned with the shoulders or ilia of the pelvis, serves the purpose of measuring spinal tilts, while the projection of a dot beam serves to measure spinal torques.

A modification of the invention, when measuring spinal torque in conjunction with an anatometer, includes an adjustably positioned mirror on the shoulder or pelvic girdle facing the wall chart, and a laser dot beam source on the center of the wall chart projecting a laser dot beam to the mirror that is reflected to the wall chart for measuring spinal torque.

A further modification of the invention is a method and apparatus for analyzing and measuring posture abnormalities, and includes a laser source for projecting a vertically extending laser line beam toward a side of the patient, and aligning the beam with the ankle as a reference, and observing any deviation of the hip, shoulder and ear from the line beam.

The measurement of spinal tilt and torque before and after treatment demonstrates the effectiveness of the chiropractic treatment given to a patient.

The determination of the type of adjustment to make on a patient requires the taking of precise cervical X-rays to determine the subluxation/misalignment of the vertebrae. Usually by adjusting of the atlas subluxation complex, the vertebrae move to their proper position all along the spine. The muscle balancing mechanism of the spine is at the occiput (C°)-atlas (C') area. Thereafter, by use of the present invention, some further X-rays can usually be avoided to determine spinal corrections.

It is therefore an object of the present invention to provide a new and improved method and apparatus for measuring spinal distortions and posture distortions of a person to demonstrate effectiveness of chiropractic treatment and reduce the need to take some X-rays.

Another object of the present invention is to provide a method and apparatus to economically and accurately measure spinal distortions of a chiropractic patient, and, more particularly, to measure spinal tilt and spinal torque at the shoulder and pelvic areas of a patient.

Another object of the present invention is the provision of a method and apparatus for measuring the spinal distortions of a person, which includes the use of a wall chart and laser sources mounted on a patient to project line and/or dot beams onto the chart for measuring spinal tilt and spinal torque.

A still further object of the invention is the provision of a method and apparatus for measuring spinal distortions that includes a wall chart having measuring indicia, a shoulder girdle harness for mounting onto the shoulder girdle or area of a patient to project the position of the shoulder area with a laser line beam and a laser dot beam onto the chart to measure spinal tilt and spinal torque in the shoulder area.

A still further object of the invention is the provision of a method and apparatus for measuring spinal distortions that includes a wall chart having measuring indicia, a pelvic girdle harness for mounting onto the pelvic area of a patient to project the position of the pelvis with a laser line beam and a laser dot beam onto the chart to measure spinal tilt and spinal torque in the pelvic area.

A further object of the present invention is to provide a pelvic and/or shoulder girdle harness with a mirror facing a wall chart for use in conjunction with an anatometer, to coact with a laser dot beam source mounted at the center of the wall chart to project a dot beam to the mirror for measuring spinal torque.

Another object of the invention is to provide a method and apparatus to analyze and measure posture distortions or abnormal posture of a person, which includes the use of a vertically extending laser line beam projecting to a side of a patient.

Other objects, features and advantages of the invention will be apparent from the following detailed disclosure, taken in conjunction with the accompanying sheets of drawings, wherein like reference numerals refer to like parts.

DESCRIPTION OF THE INVENTION

This invention relates to the measuring of spinal distortions of a person at the shoulder area and at the pelvic area, and posture distortions of a person, and includes the use of laser light sources mounted on a patient standing in facing relationship to a wall chart so that spinal tilt or tip and/or pelvic tilt or tip, together with spinal torque, can be measured at the shoulder and/or pelvic areas of a person, and a laser source mounted laterally of a patient to project a vertically extending laser line for measuring posture distortions. The apparatus for supporting laser sources to measure spinal tilt and torque includes a shoulder girdle harness mountable on the shoulders of a person and a pelvic girdle harness mounted at the pelvic area of a person. Each of the harnesses includes one or more laser light sources for projecting generally horizontally extending laser line beams and laser dot beams to project the positions of the shoulder and pelvic areas. These beams are projected onto the wall chart having measuring indicia for measuring spinal tilts and spinal torques.

The shoulder and pelvic girdle harnesses are adjustable for persons of various sizes, and are constructed so as to be mountable on the shoulder and pelvic areas of a person to produce accurate spinal tilt and torque measurements.

A single laser beam light source may be provided which is adjustable to produce a laser line beam, a laser dot beam, or both. Individual laser sources may be provided that only produce a laser line beam or only a laser dot beam.

A modification of the invention, when using the laser system with an anatometer, includes the use of a mirror mountable on the pelvic girdle harness that coacts with a laser source mounted at the wall chart projecting a laser dot beam to the mirror that is reflected back to the wall chart for measuring spinal torque or twist. It will be appreciated that such a mirror and laser source could also be used in conjunction with the shoulder girdle.

Referring now to the drawings, and particularly to FIGS. 1–5, the apparatus of the invention for measuring spinal tilt and torque includes a shoulder girdle harness 15 mounted at the shoulder area 16 of a person or patient 17 and a pelvic girdle harness 20 mounted at the pelvic area 21 of the person 17. Each of the harnesses is provided with laser light sources as described below for coacting with a wall chart 25 mounted on a substantially vertical wall to measure spinal tilts and torques.

Figure 1:
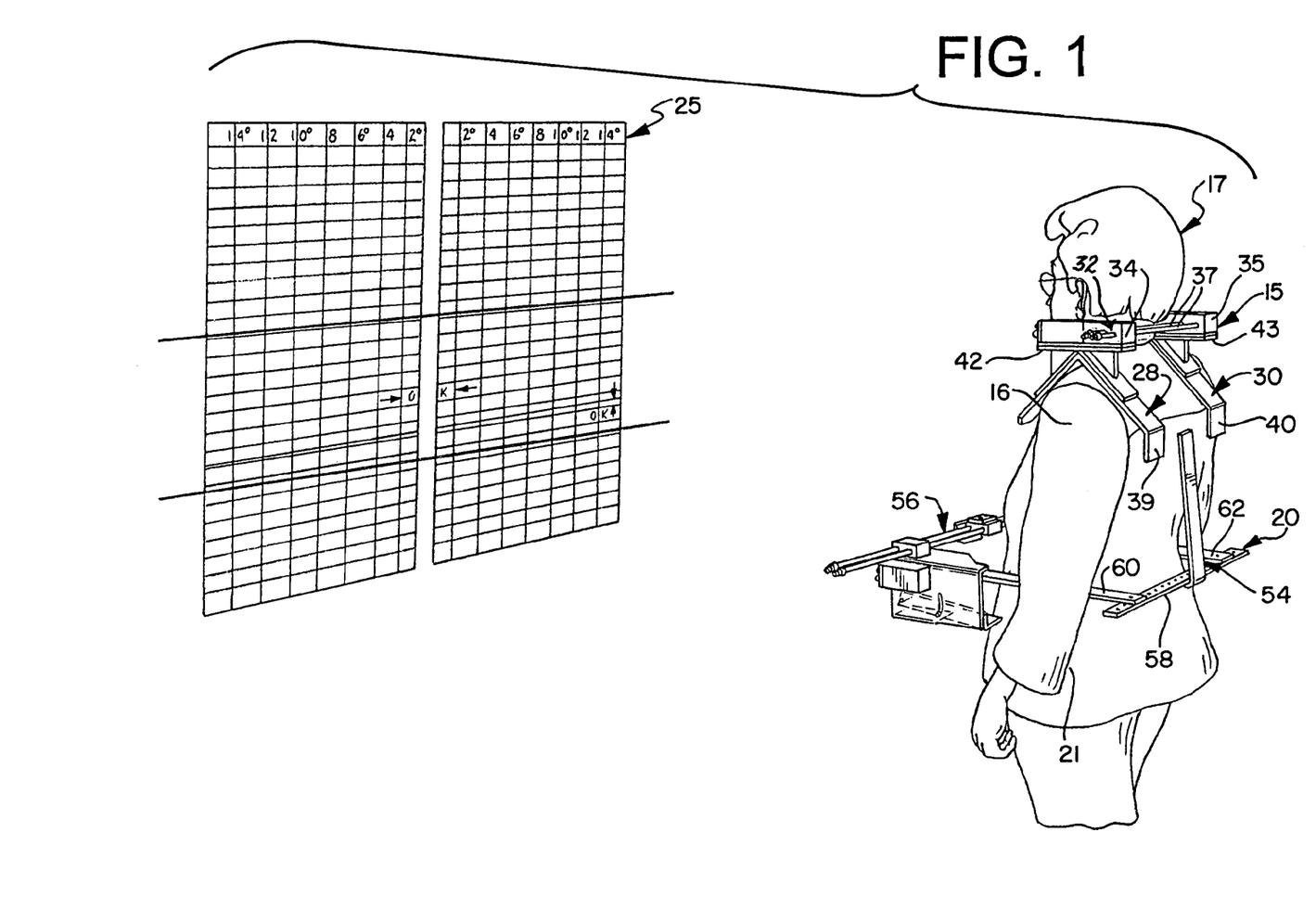
FIG. 1 is a perspective view of a person having a shoulder girdle harness mounted in place at the shoulder area of a person and a pelvic girdle harness mounted in place at the pelvic area facing a wall chart and showing on the wall chart laser line beams for measuring spinal tilt at the shoulder and pelvic areas and laser dot beams for measuring spinal torque at the shoulder and pelvic areas.
Figure 2:
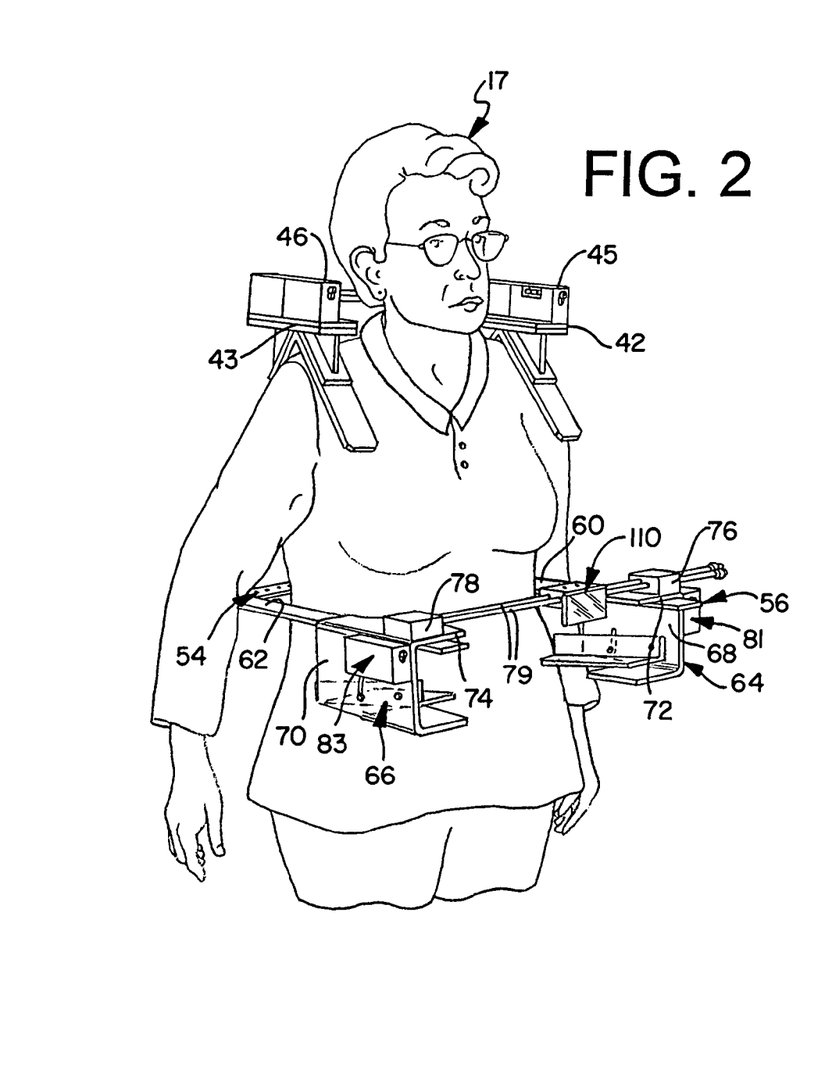
FIG. 2 is a front perspective view of the person in FIG. 1 having shoulder and pelvic girdle harness mounted in place.
Figure 4:
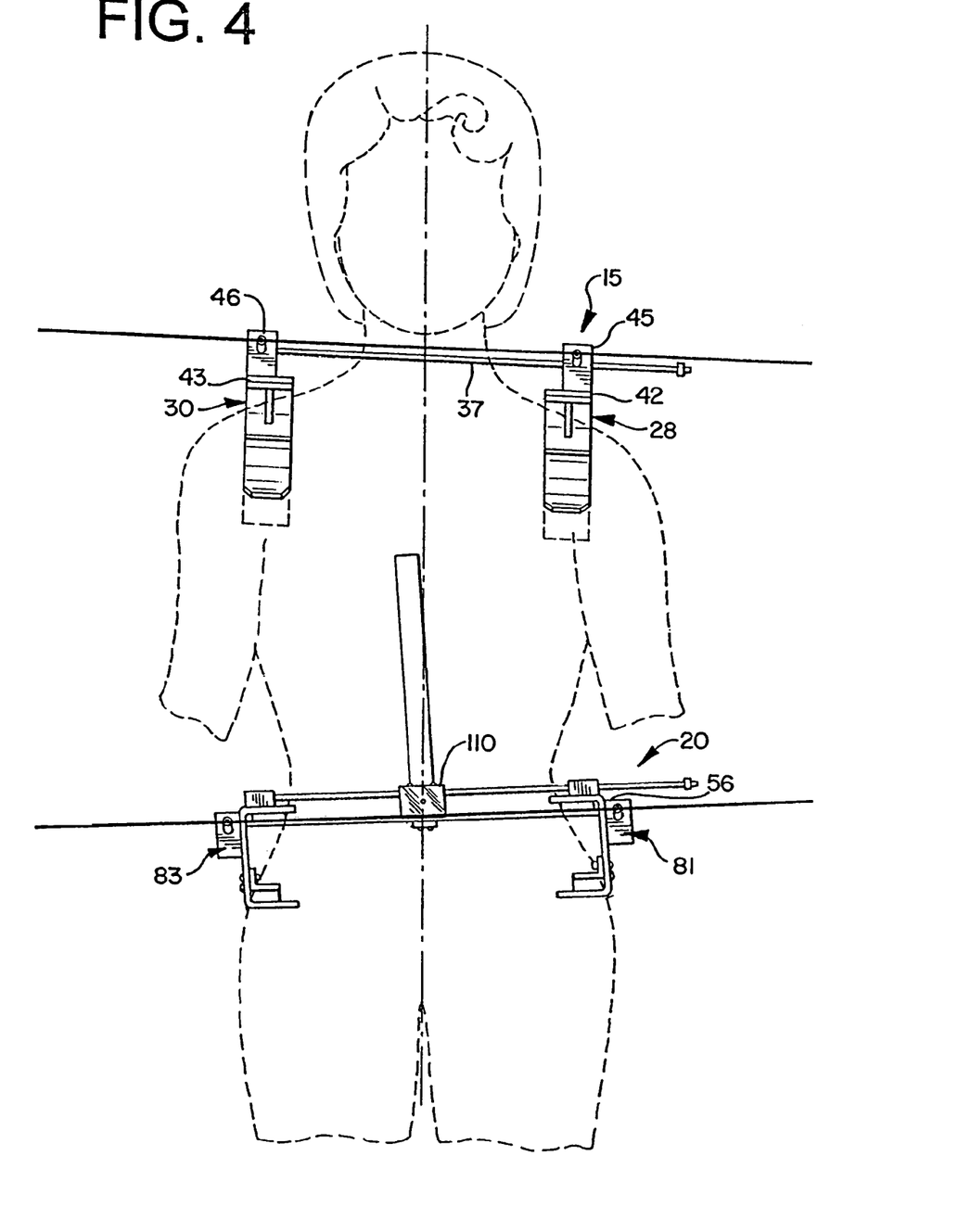
FIG. 4 is a front elevational view of a person in phantom and having mounted thereon a shoulder girdle harness and a pelvic girdle harness to illustrate the use of a laser source for producing laser line beams to measure spinal tilt.

The shoulder girdle harness 15 includes a pair of inverted V-shaped frame members 28 and 30 adapted to rest on the shoulders of a person and interconnected by an adjustable bar mechanism 32. The bar mechanism includes opposed blocks 34 and 35, respectively attached to the inverted V-shaped frame members 28 and 30. A pair of rods 37 is anchored at one end to the block 35 and slidably moved in bore holes of the block 34 whereby the blocks may be adjustably spaced apart to fit the shoulders of a particular patient by sliding the block 34 along the rods 37 toward or away from the block 35.

In order to assist in stabilizing the position of the inverted V-shaped frame members 28 and 30 of the girdle on a person, the lower ends of the V-shaped member at the rear of the harness are bent at an angle to define stabilizing tabs or members 39 and 40 that bear against or near the back of the person.

Figure 5:
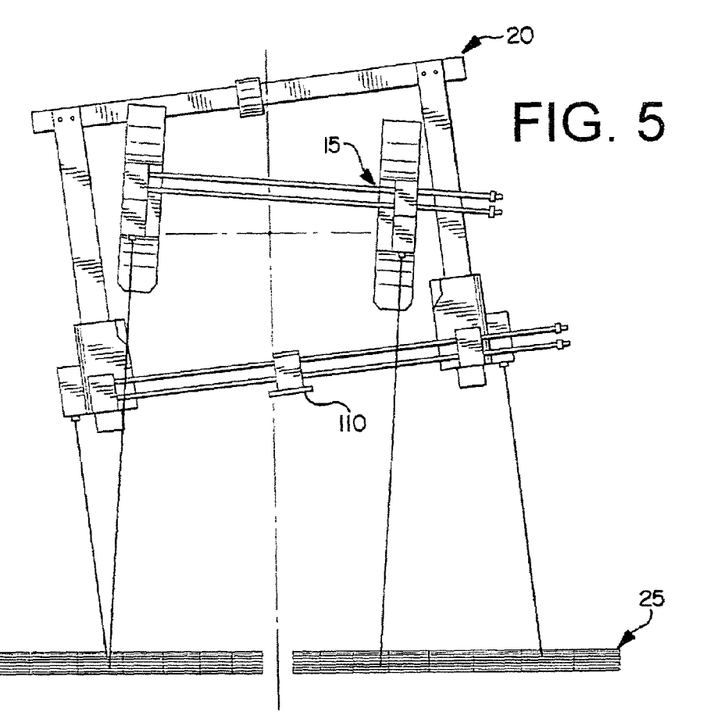
FIG. 5 is a top plan view of a shoulder girdle harness and a pelvic girdle harness to illustrate a projection of laser dot beams for measuring spinal torques at the shoulder and/or pelvic areas and showing the wall chart having an exaggerated thickness.
Figure 5A:
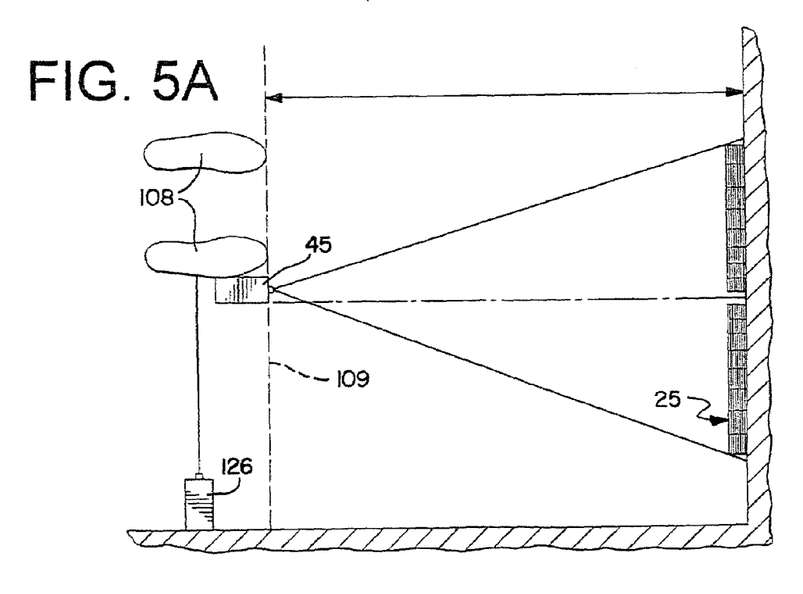
FIG. 5A is an overhead schematic view illustrating the relationship of a patient as positioned facing the wall chart and showing the wall chart having an exaggerated thickness.

The blocks 34 and 35 are mounted on generally horizontally extending bars or plates 42 and 43 at the front and top of the harness. While two laser light sources are shown on the shoulder girdle harness, it will be appreciated that only one need be used to project a line or dot beam when adjustable to do so, or one of the light sources may only project a line beam while the other may only project a dot beam. It should also be appreciated that each of the light sources may selectively project a line beam or a dot beam. Since the light sources are mounted on the harness at one side thereof, it will be appreciated that the patient, when facing the wall chart, will be positioned laterally of the center of the chart so that the light source will be aligned with the center of the chart, as shown in FIG. 5A.

Figure 3:
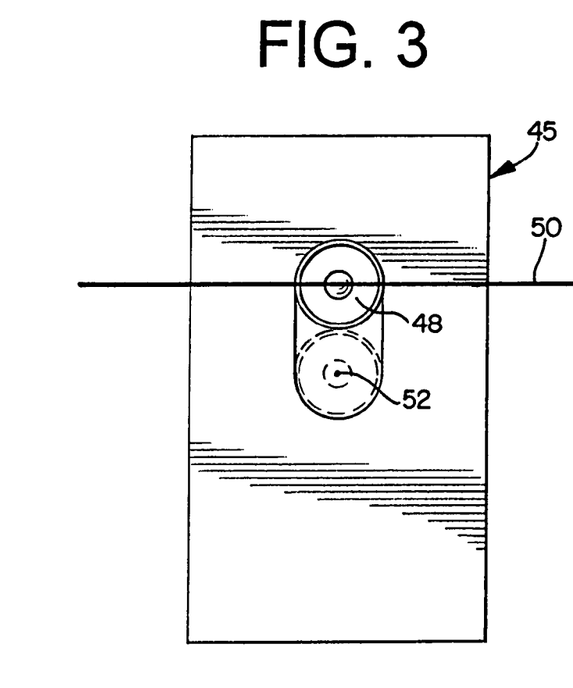
FIG. 3 is a greatly enlarged front elevational view of a laser beam source that is adjustable for producing either a laser line beam or a laser dot beam by operating a slide aperture.

The enlarged front view of a light source is shown in FIG. 3 is of the type that would be adjustable, and is generally indicated by numeral 45. Looking at the light source from the front, it is generally box-shaped, but it could be of any suitable shape, and further includes an aperture 48 slidable between the position shown in solid lines to project a laser line beam 50, or to a position shown in phantom to project a laser dot beam 52. It will be appreciated that any suitable laser light source may be provided that is adjustable to project either a line beam or a dot beam. Any type of low to intermediate power laser sources may be used, such as a diode laser that emits a red beam of light like that used in pocket or pen-like pointing lasers. Any suitable beam color may be chosen.

While the shoulder girdle harness 15 is shown to include the interconnection of opposed shoulder engaging frame members 28 and 30 by use of a pair of slide rods, it will be appreciated that a single slide bar may be provided for interconnecting the shoulder engaging members and for allowing adjustment of the spacing between the members or some other mechanism that would allow adjustments. While it is more practical to provide a shoulder girdle harness that is adjustable, it will be appreciated that non-adjustable shoulder girdle harness could be used, in which case a plurality of sizes would be available for fitting on patients of various sizes.

The pelvic girdle harness 20, like the shoulder girdle harness, is adjustable for fitting on patients of various sizes. It will be appreciated that within the scope of the invention, while it is preferred to include both the shoulder girdle harness for measuring spinal distortions at the upper end of the spine, and a pelvic girdle harness for measuring distortions at the lower end of the spine, where it may occasionally be necessary to take measurements only at the shoulder area or the pelvic area, only one of the girdle harnesses need be used.

The pelvic girdle harness 20 includes a U-shaped pelvic frame 54 and a laser source support member 56 which coact to be supported on the ilia of a patient. The U-shaped frame is adjustable and includes a crossbar 58 extendable along the back of a patient at a generally horizontal position and forwardly extending pelvic engaging bars or arms 60 and 62 that engage on the ilium of each of the hips so that the U-shaped frame will be positioned on the ilia of a person to measure the spinal tilt and torque at the pelvic area. The rear ends of the bars 60 and 62 are connected to the crossbar 58 by a suitable fastener that allows the adjustable positioning of the arms along the crossbar for fitting the U-shaped frame to a patient. A number of holes or other devices can be provided in the crossbar 58 so that the arms 60 and 62 can be adjustably secured therealong with a suitable fastener. Any other type of adjustable mechanism may be provided to allow the adjustable spacing between the arms along the crossbar to facilitate mounting on the ilia of a person.

The laser source support member 56 includes spaced apart opposed laser source mounting plates 64 and 66. The plates in the illustrated embodiment are channel shaped, with the open ends of the channels facing each other, although they may be otherwise suitably formed to coact with the arms. Each of the mounting plates respectively includes generally vertically extending plates 68 and 70 and generally horizontally extending flanges 72 and 74. Blocks 76 and 78 are respectively mounted on the upper side of the flanges 72 and 74 for receiving a pair of slide bars 79 that interconnect the opposing laser source mounting plates together. More specifically the slide bars 79 are anchored at one end to the block 78 and are slidably engageable in bore holes of block 76. Accordingly, the space between the mounting plates 74 and 76 can be adjustably positioned in order to properly fit the laser source support member onto the arms 60 and 62 of the U-shaped pelvic frame 54. While a pair of slide bars is shown, any suitable number may be provided like in the shoulder girdle.

Laser light sources 81 and 83 are respectively mounted on the outside surfaces of the generally vertically extending plates 68 and 70. These light sources will be of the same type as the light sources 45 and 46 on the shoulder girdle harness, and each may be adjustable to project a line beam or a dot beam. Also, the light sources may only be structured to either project a line beam or a dot beam. It should be appreciated that only one laser light source may be provided if it is adjustable to project a line beam or a dot beam.

Figure 6:
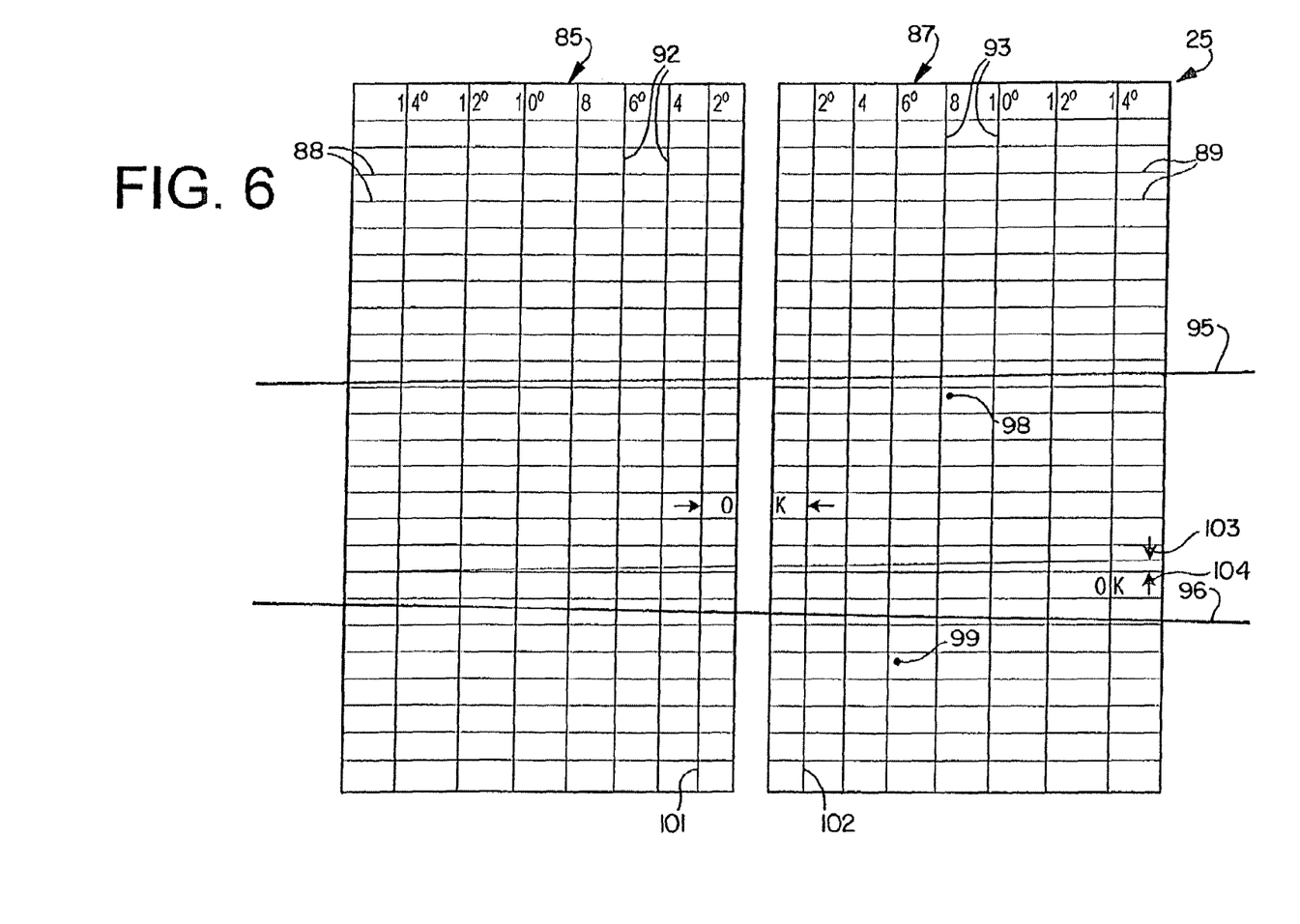
FIG. 6 is a front elevational view of a wall chart according to the invention having indicia for measuring spinal tilt and spinal torque and illustrating laser line beams and laser dot beams on the chart.

Referring to FIG. 6, the wall chart 25 is composed of left and right sections 85 and 87 that are equal and opposite to each other. These charts include a plurality of equally spaced apart horizontally extending lines 88 and 89 and a plurality of vertically extending lines 92 and 93. The horizontally extending lines 88 and 89 are aligned with each other and vertically spaced apart equally for measuring spinal tilt in conjunction with a degree measuring instrument like the protractor shown in FIGS. 10 and 11 and described hereafter, while the vertically extending lines 92 and 93 are variably spaced apart to measure the spinal torque. Spinal tilt is preferably measured in degrees by the use of the protractor, and spinal torque is preferably measured in degrees that are gauged by the lines on the chart as spaced according to the positioning of the patient, although any suitable units of measurements may be used.

Spinal tilt is measured by using the projected laser line beam such as the line beam 95 from the shoulder girdle harness and/or the line beam 96 from the pelvic girdle harness in degrees, while spinal torque may be measured in degrees or just reference numbers, such as by the illustrated dot beam 98 and the dot beam 99. Any suitable type of measuring units may be utilized in accordance with the scope of the invention. With respect to the spinal torque measurements, they constitute a composite value of the comparative distances from a vertical reference line to the line beam at the left chart segment 85 and the right chart segment 87, taken at the same distance from the center to a suitable vertical line at each side, as seen in FIG. 6. Also, the distance the patient is spaced from the chart along with any translation at the patient's body lateral to their feet is considered. It should be appreciated that the center of a patient's body must be positioned the same when taking before and after measurements.

The spinal torque measurement is taken by a dot beams along the vertical degree lines. These degree lines are variably spaced apart and calibrated to provide a substantially accurate spinal torque value. For example, as shown in FIG. 6, the dot beam 98 from the shoulder girdle harness is at about eight degrees, or a suitable measured value, on the right hand section of the chart, while the dot beam 99 from the pelvic girdle harness is about six degrees, or a suitable measured value, at the right hand section of the chart. If the dot beams fall within the lines 101 and 102, the torque values may be acceptable, depending on the desired values of the clinician treating a patient. Similarly, if the line beam falls between the arrows 103 and 104, the tilt value is acceptable, depending on the desired values of the clinician. However, the standard for acceptability of tilt and torque may be determined by the user.

It will be appreciated that the chart 25 may be formatted on a wall in any suitable manner. For example, since the chart 25 includes a left section 106 and a right section 107 wherein the sections are aligned with each other so that the horizontal indicia lines 88 and 89 are in alignment with each other, the chart may be permanently printed or otherwise placed on the wall. Further, the charts may be printed on paper or plastic material that is rollable into a roll for purposes of shipping and which can then be unrolled and hung on a wall. In any event, preferably the face of the chart is provided with an anti-glare finish or a suitable finish that allows the ready reading of the laser line and/or dot beams. It should also be recognized that the color of the charts may be of any suitable type. For example, the vertical and horizontal lines may be black or any suitable color.

Figure 7:
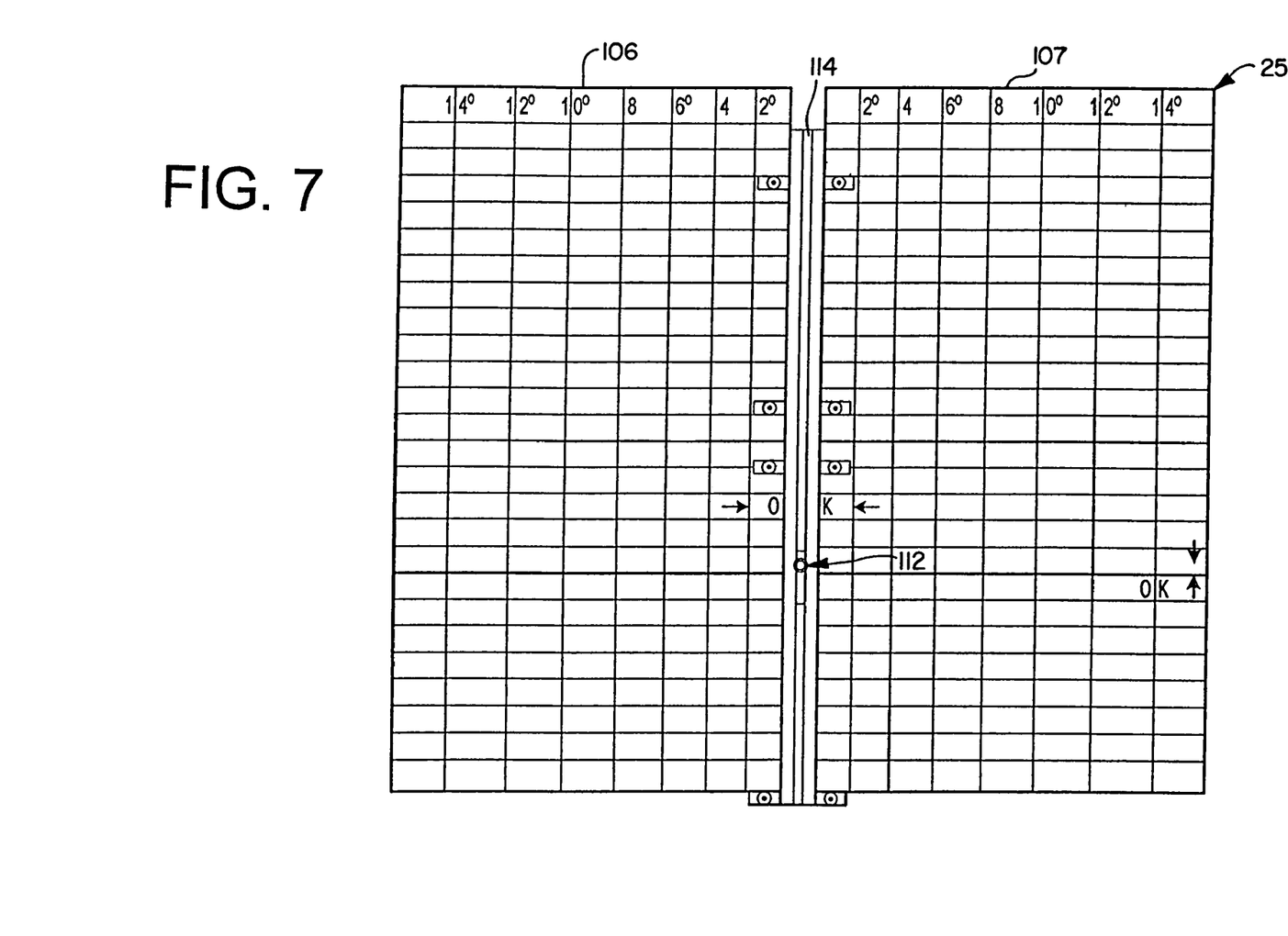
FIG. 7 is a modified wall chart according to the invention which includes a laser light source for projecting a laser dot beam toward a patient standing in front of the chart and having a mirror mounted on the pelvic girdle harness to measure spinal torque.

A modified chart is shown in FIG. 7 which also coacts with a modification of the pelvic girdle harness, and is used in conjunction with an anatometer with the patient properly positioned on the anatometer so that the center of the patient is aligned with the center of the chart. As seen in FIGS. 3 and 4, a mirror 110 is mounted on the rods 78 of the pelvic girdle harness and slidable therealong to position the mirror such that the laser beam will hit the mirror and reflect back to the chart. This mirror coacts with a laser source 112 mounted on and movable along a vertical track 114 that in turn is mounted on the wall between the chart sections 106 and 107. The mirror is positioned substantially directly opposite the laser source so that the laser dot beam projected from the laser source 112 hits the mirror in the center of the pelvic girdle harness and the patient is standing about six to eight feet from the chart and facing the chart. This laser source projects a dot beam to the mirror which is reflected and projected to the chart for measuring spinal torque. The reflected dot beam will be centered on the chart when the torque value is zero. This combination of the wall mounted laser source and a mirror is optional and defines another method of measuring spinal torque when an anatometer is available, as explained below.

A method of measuring spinal tilt and/or spinal torque at the shoulder area with the shoulder girdle harness and/or at the pelvic area with the pelvic girdle harness involves the steps of suitably mounting a shoulder girdle harness onto the shoulder area of a person, as illustrated in FIGS. 1, 2 and 4. Further, it involves the step of mounting a pelvic girdle harness on the pelvic girdle or area of a person, as illustrated in the same Figures. It will be appreciated here that the invention optionally includes the use of the shoulder girdle harness and the pelvic girdle harness, depending upon the information desired by the chiropractor in connection with a particular patient being treated. However, it is preferable that measurements be taken at both the shoulder area and the pelvic area to determine the spinal tilt and torque at both areas.

When mounting the shoulder girdle harness on a person, the inverted V-shaped members 28 and 30 are adjusted to be spaced apart so that they comfortably rest on the shoulders of the patient in a manner illustrated in FIGS. 1, 2 and 4. Similarly, the mounting of the pelvic girdle harness includes the adjustable positioning of the bars 60 and 62 along the crossbar 58 to fit at the pelvic area of the patient and rest on the ilia of the patient, and thereafter the adjustable spacing of the laser source mounting plates 64 and 66 along the slide bar 79, so that the mounting plates will rest properly on the forwardly extending bars or arms of the U-shaped pelvic frame 54.

Thereafter, the patient will be appropriately positioned relative to the wall chart in alignment with the center of the chart and spaced from the chart, as illustrated in FIG. 5A, where a patient's toes 108 are aligned with a floor line 109 that extends parallel to the wall chart 25. It should be appreciated that a properly placed line or the like could be provided for aligning the heels of a person. Since the laser source is mounted at one side of the shoulder and pelvic girdles, the patient will be positioned facing the chart and to the right or left of the center of the chart depending on the side of the harness the laser light or source is mounted so that the laser source is substantially aligned with the center of the chart. Thus, the patient will be positioned off-center to the chart. The laser light source will next be engaged to project the desired laser light beams to the chart 25 with respect to the shoulder girdle harness for taking the desired measurements.

While the laser light sources are shown as above mentioned, it may only be necessary for a single laser light source to be used, provided that the particular light source can be used in the modes of projecting a line beam or a dot beam. Optionally, where two sources are used, one of the laser light sources may be used to project only a line beam, while the other may be used to project only a dot beam. It is also possible that both laser light sources may, at the same time, project laser line beams or laser dot beams. The laser sources are squared with the shoulder girdle harness so as to produce meaningful values on the chart. Similarly, the pelvic girdle harness, while including a pair of laser light sources, may only need to have a single laser light source so long as the single laser light source is capable of projecting both a laser line beam and a laser dot beam.

Further, spinal torque can be measured when the pelvic girdle harness is modified to include the mirror 110 to coact with a laser light source at the wall in the center of the chart for projecting a dot beam, as shown in FIG. 7.

Figure 8:
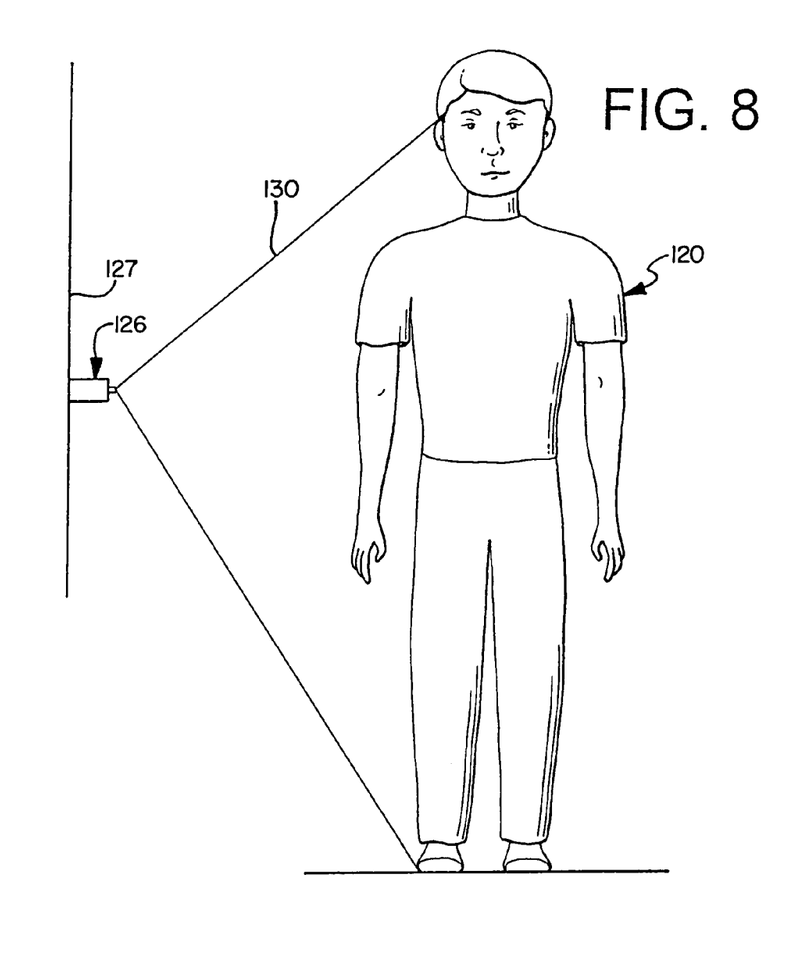
FIG. 8 is a front elevational view of a person and an apparatus for measuring posture distortions.
Figure 9:
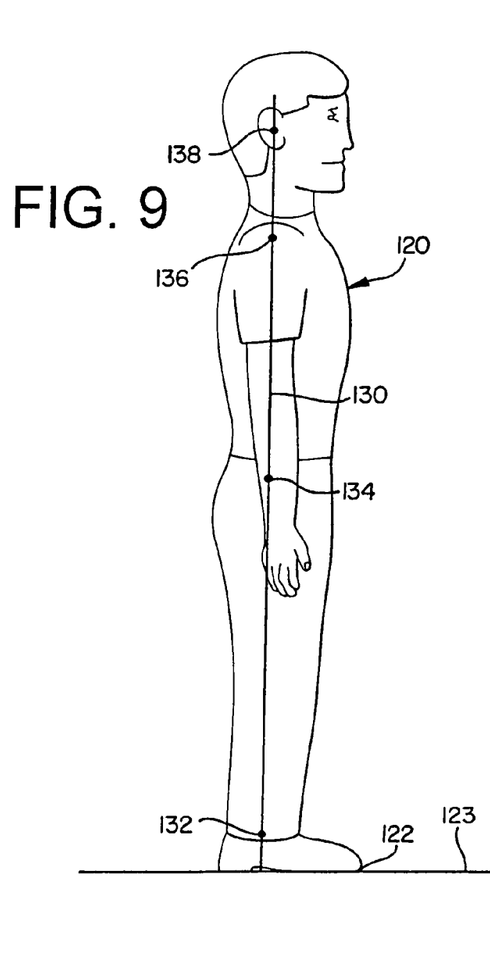
FIG. 9 is a side elevation of a person illustrating the use of a vertically extending laser line beam for measuring posture.

The present invention also includes the method and apparatus for analyzing and measuring posture abnormalities before and after chiropractic treatment by use of laser technology. As seen in FIGS. 8 and 9, the apparatus includes means for positioning a patient at a predetermined location and a laser source for projecting a vertical line beam to one side of the patient. More particularly, a patient 120 is shown in FIGS. 8 and 9 positioned in standing relation such that the toes of the person are aligned with and touch a line 122 on the floor 123 so that a laser source 126 mounted on a wall or stand 127 can project a vertical line beam 130 parallel to the floor line 122, and onto the patient. This is also shown in FIG. 5A. It will be appreciated that after the patient is positioned at the line, the laser source can be moved for the line beam to strike the ankle of the patient, as the ankle joint 132 is the reference point for positioning the laser source. The optimum posture will be when the hip joint, designated as 134, is over the ankle joint, and the shoulder joint, designated as 136, is over the hip joint, and the ear, designated as 138, is over the shoulders. Thus, substantially perfect posture will produce vertical alignment of the ear, shoulder, hip and ankle along either side of the body with the patient looking straight ahead and the head in an up position.

Markers may be placed on the patient during posture analysis so that once a beam is projected onto the patient and aligned with the ankle, distances between the beam and markers on the hip, shoulder and ear can be measured. A substantially perfectly balanced spine will produce an optimum posture for a patient when the ear, shoulder and hip align with the ankle.

Accordingly, the method of analyzing and measuring posture will include positioning of a patient on a floor line, locating a laser source capable of projecting a vertical laser line beam at one side of the patient to project the line beam at the patient, and then aligning the beam with the ankle as a reference point to measure the positions of the hip, shoulder and ear relative to the beam, and determine if the sagittal posture is optimum for the patient.

Figure 10:
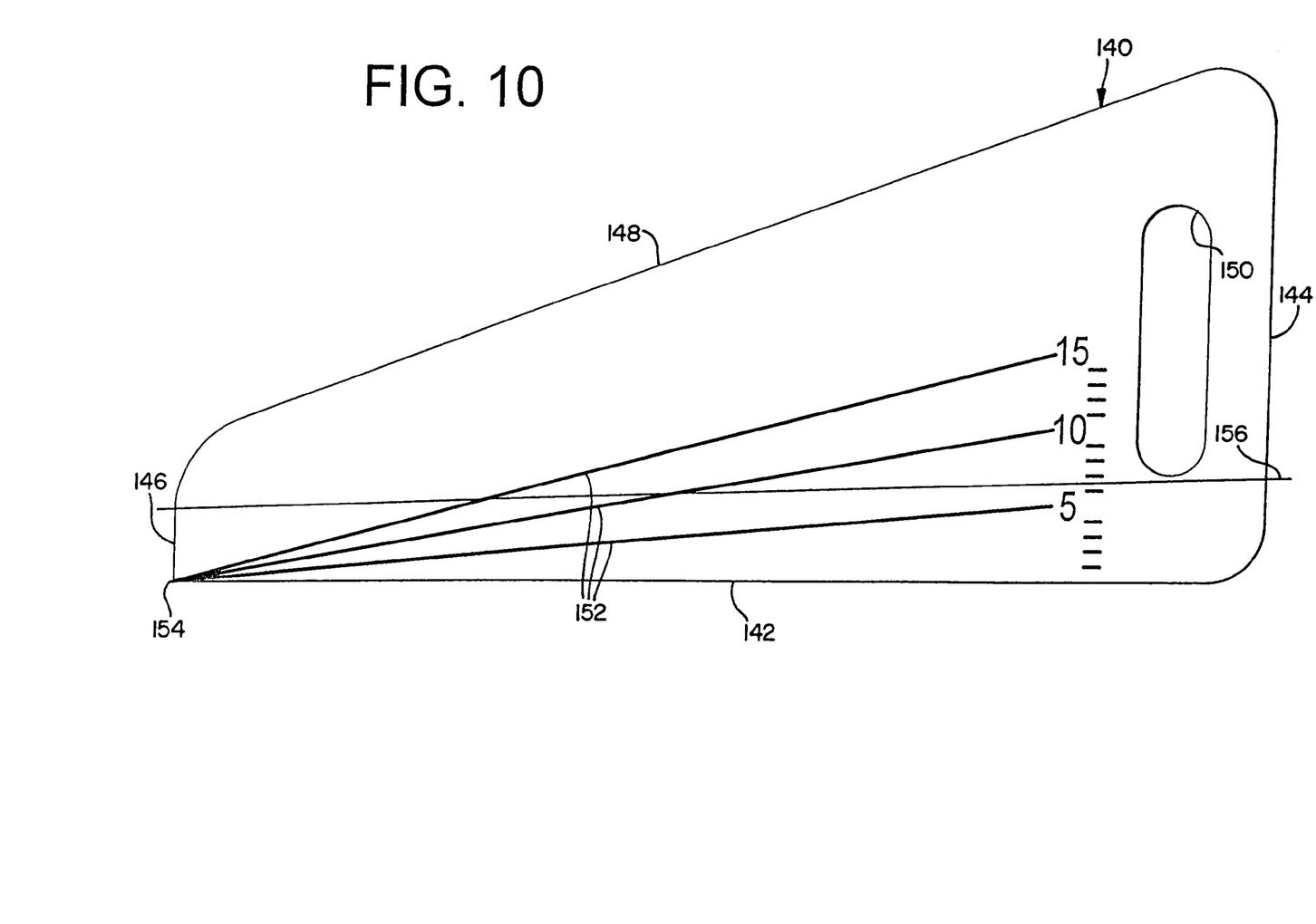
FIG. 10 is an elevational view of a unique protractor for use in measuring the degrees of spinal tilt at the wall chart.
Figure 11:
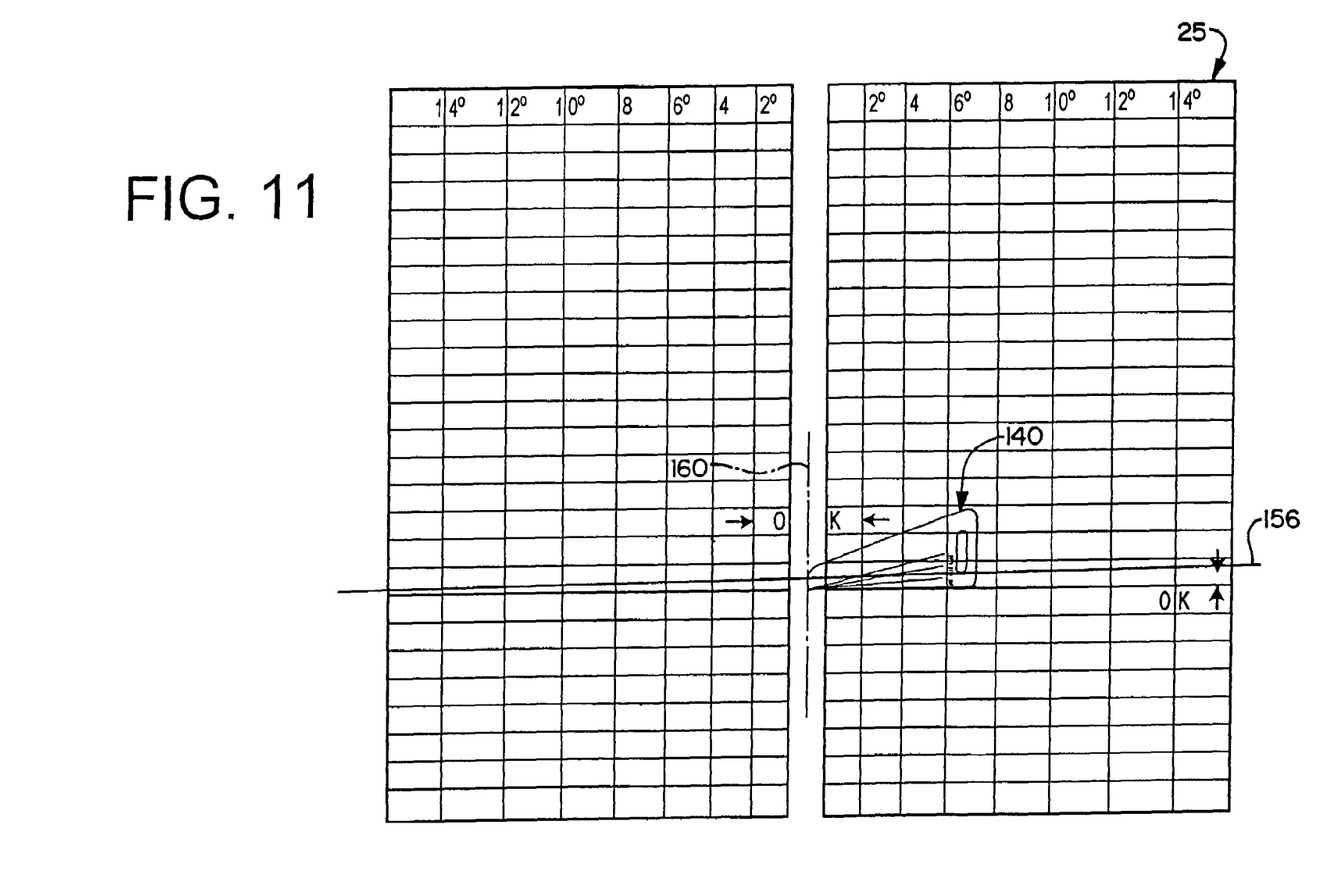
FIG. 11 is an elevational view of a wall chart with a laser line beam and illustrating the use of the protractor in FIG. 10 to measure spinal tilt.

The present invention also includes a specially designed protractor for coacting with the wall chart and the laser line beam for measuring tilt of a patient's body at the shoulder area or the pelvic area. This protractor is shown in FIGS. 10 and 11. In FIG. 11 the placement of the protractor on the wall chart is illustrated for measuring the body tilt. As seen in FIG. 10, the protractor is shaped like a handsaw and is generally identified by the numeral 140 which includes a base edge 142, a vertical edge 144 at one end which extends perpendicular to the base edge 142, an opposing shorter vertical edge 146 also extending perpendicular to the base edge 142 and in parallel relation to the base edge 144, and an angular edge 148 opposed to the base edge 142 slanting down from the vertical edge 144 to the vertical edge 146, and interconnecting to the opposing vertically extending edges 144 and 146. This configuration defines the protractor having a nose end at the edge 146 and a handle end at the edge 144. A vertically extending hand opening 150 is disposed at the handle end of the protractor for defining a portion engageable by the hand of a person to manipulate the end of the protractor against the wall chart, as seen in FIG. 11, and in connection with a generally horizontally extending reference line and the horizontally projected line beam.

Suitable indicia is provided on the face of the protractor to measure tilt in degrees from the horizontal as illustrated. Degree value lines of 5, 10 and 15 are illustrated on the protractor 140, as seen in FIG. 11. These values are represented by lines 152 intersecting with the left edge of the base line 142 and the bottom or lower end of the vertical edge 146 at 154. Further, degree graduation lines are provided between the numerals 5, 10 and 15 at the handle end of the protractor to facilitate reading the spinal tilt value.

When measuring tilt of the body of a person, as represented by the generally horizontally extending laser line beam shown to be 156 in FIG. 11, the protractor is positioned on the wall chart such that the bottom or base edge 142 of the protractor aligns with the nearest horizontal reference line on the chart below the laser line beam, while the left side edge 146 is aligned with the center line 160 of the wall chart. As illustrated most clearly in FIG. 10, the body tilt value is at about 6.5 degrees. As noted in FIG. 11, the protractor is positioned on the side of the chart where the largest distance between a chart line and the line beam appears. Thus, the protractor is used to coact with the wall chart to measure body tilt in degrees.

From the foregoing it will be appreciated that the method and apparatus of the invention through the unique use of laser beam technology produces a guide for the chiropractor to demonstrate to the patient the accurate improvement of spinal tilt and torque once adjustment procedures have been undertaken. By taking measurements before and after adjustment procedures, it can be demonstrated to the patient and the treating chiropractor by an efficient process how the spinal column has been corrected to remedy subluxations of the vertebrae, thereby reducing the need to take some further X-rays. The present invention also includes a method and apparatus for determining and measuring abnormal posture distortions. Further, the invention includes a unique protractor for coacting with the wall chart and the laser line beam to measure body tilt.

It will be understood that modifications and variations may be effected without departing from the scope of the novel concepts of the present invention, but it is understood that this application is to be limited only by the scope of the appended claims.

The invention claimed is:

1. Apparatus for measuring spinal distortions at the shoulder area of a person standing upright on his or her feet at a predetermined location and orientation adjacent to a generally vertically extending wall comprising:
 a chart mounted on said wall opposite said person and having indicia thereon for measuring spinal tilt and torque, and
 a shoulder girdle harness for mounting onto the shoulders of said person,
 said shoulder girdle harness having laser means for projecting a line beam onto said chart for coacting with the indicia on said chart to measure shoulder tilt and/or a dot beam for projecting onto said chart for coacting with said indicia for measuring spinal torque.

2. The apparatus of claim 1, wherein said laser means includes a laser source for projecting a line beam onto the chart, and a laser source for projecting a dot beam onto the chart.

3. The apparatus of claim 1, wherein said laser means includes a laser source adjustable to project a line beam or a dot beam onto the chart.

4. The apparatus of claim 1, wherein said shoulder girdle harness is adjustable for mounting on persons of various sizes.

5. The apparatus of claim 1, which further includes means coacting with the chart and the line beam for measuring shoulder tilt.

6. The apparatus of claim 5, wherein said measuring means includes a protractor.

7. The apparatus of claim 6, wherein said protractor includes a base edge, opposed vertical side edges, an upper edge connecting the side edges and slanting down from one vertical edge to the other defining one side edge longer than the other, a handle at the longer side edge, and indicia on the protractor for indicating spinal tilt in units of measurement.

8. Apparatus for measuring spinal distortions at the pelvic area of a person standing upright on his or her feet at a predetermined location and orientation adjacent to a generally vertically extending wall comprising:

a chart mounted on said wall having indicia for measuring pelvic tilt and torque, and a pelvic girdle harness for mounting onto the pelvic area of a said person;

said pelvic girdle harness having laser means for projecting a line beam onto said chart for coacting with the indicia on the chart to measure pelvic tilt and/or a dot beam for projecting onto said chart for coacting with said indicia for measuring pelvic torque.

9. The apparatus of claim 8, wherein said laser means includes a laser for projecting a line beam onto the chart, and a laser for projecting a dot beam onto the chart.

10. The apparatus of claim 8, wherein said laser means includes a laser adjustable to project a line beam or a dot beam onto the chart.

11. The apparatus of claim 8, wherein said pelvic girdle harness is adjustable for mounting on persons of various sizes.

12. The apparatus of claim 8, which further includes means coacting with the chart and the line beam for measuring pelvic tilt.

13. The apparatus of claim 12, wherein said measuring means includes a protractor.

14. The apparatus of claim 13, wherein said protractor includes a base edge, opposed vertical side edges, an upper edge connecting the side edges and slanting down from one vertical edge to the other defining one side edge longer than the other, a handle at the longer side edge, and indicia on the protractor for indicating pelvic tilt in units of measurement.

15. Apparatus for measuring spinal distortions at the shoulder and pelvic areas of a person standing upright on his or her feet at a predetermined location and orientation adjacent to a generally vertically extending wall comprising:

a wall chart having indicia for measuring spinal tilt and torque;

a shoulder girdle harness for mounting on the shoulders of said person;

said shoulder girdle harness having laser means for directing a laser line beam onto the chart to measure spinal tilt at the shoulder area and a laser dot beam to measure spinal torque at said shoulder area, and a pelvic girdle harness for mounting on the pelvic area of said person to measure spinal tilt and torque at the pelvic area, said pelvic girdle harness having laser means for directing a laser line beam onto the chart to measure spinal or pelvic tilt and a laser dot beam to measure spinal torque at said pelvic area.

16. The apparatus of claim 15, wherein said laser means on the shoulder girdle harness includes a laser source for projecting a line beam and a laser source for projecting a dot beam.

17. The apparatus of claim 15, wherein said laser means on the pelvic girdle harness includes a laser source for projecting a line beam and a laser source for projecting a dot beam.

18. The apparatus of claim 15, wherein said laser means on the shoulder girdle harness includes a laser source adjustable to project a generally horizontally extending line beam or a dot beam.

19. The apparatus of claim 15, wherein said laser means on the pelvic girdle harness is adjustable to project a generally horizontally extending line beam or a dot beam.

20. The apparatus of claim 15, wherein said shoulder girdle harness is adjustable to fit on persons of various sizes.

21. The apparatus of claim 15, wherein said pelvic girdle harness is adjustable to fit on persons of various sizes.

22. The apparatus of claim 15, wherein said shoulder and pelvic girdle harnesses are adjustable to fit persons of various sizes.

23. The apparatus of claim 15, wherein said chart includes a plurality of horizontally extending and vertically spaced apart lines for measuring tilt, and a plurality of vertically extending and horizontally spaced apart lines to measure torque.

24. The apparatus of claim 23, wherein said chart includes a vertically extending median and vertically extending and horizontally spaced apart lines on opposite sides thereof.

25. The apparatus of claim 24, wherein the vertically extending lines are variably spaced apart to measure torque in degrees or numbers.

26. The apparatus of claim 23, wherein the horizontally extending lines are incrementally vertically spaced apart to measure tilt in metric or English units.

27. The apparatus of claim 15, which further includes means coacting with the chart and the line beam for measuring spinal tilt.

28. The apparatus of claim 27, wherein said measuring means includes a protractor.

29. The apparatus of claim 28, wherein said protractor includes a base edge, opposed vertical side edges, an upper edge connecting the side edges and slanting down from one vertical edge to the other defining one side edge longer than the other, a handle at the longer side edge, and indicia on the protractor for indicating spinal tilt in units of measurement.

30. The apparatus of claim 15, which further includes a mirror on one of the shoulder or pelvic girdle harnesses facing the wall chart, and a laser source at the wall chart coacting with the mirror to project a dot beam to the mirror for reflection to the chart to measure spinal torque.

31. The method of measuring spinal distortions at the shoulder area of a person standing upright on his or her feet at a predetermined location and orientation adjacent to a generally vertically extending wall, which comprises the steps of:

mounting a chart on said wall opposite to said person wherein the chart includes horizontally extending and vertically extending lines, mounting a shoulder girdle harness onto the shoulder area of said person, wherein the shoulder girdle harness includes means for projecting a laser line beam and a laser dot beam onto the chart for measuring spinal tilt and torque, positioning said person in aligned and spaced relation to the chart and oriented so that the laser line and dot beams strike the chart to measure spinal tilt and torque, and reading the spinal tilt and torque values.

32. The method of measuring spinal distortions at the pelvic area of a person standing upright on his or her feet at a predetermined location and orientation adjacent to a generally vertically extending wall, which comprises the steps of:

mounting a chart on said wall wherein the chart includes horizontally extending and vertically extending lines, mounting a pelvic girdle harness onto the pelvic area of said person, wherein the pelvic girdle harness includes means for projecting a laser line beam and a laser dot beam onto the chart for measuring pelvic or spinal tilt and torque, positioning said person in aligned and spaced relation to the chart and oriented so that the laser line and dot beams project onto the chart to measure spinal tilt and torque, and reading the spinal tilt and torque values.

33. The method of measuring spinal distortions at the shoulder and pelvic areas of a person standing upright on his or her feet at a predetermined location and orientation adjacent to a generally vertically extending wall, which comprises the steps of:

mounting a chart on said wall wherein the chart includes spaced apart horizontally extending and vertically extending indicia lines, mounting shoulder and pelvic girdle harnesses on a patient, wherein the girdle harnesses include means for projecting laser line beams onto the chart to coact with the horizontal lines to measure spinal tilts, and laser dot beams onto the chart to coact with the vertical lines to measure spinal torque, positioning said patient in aligned and spaced relation to the chart, engaging said laser beams projecting means to project the beams, and reading the spinal tilt and torque values.

34. The method of measuring spinal distortions at the shoulder and pelvic areas of a person standing upright on his or her feet at a predetermined location and orientation adjacent to a generally vertically extending wall, which comprises the steps of:

mounting a chart on a substantially vertically extending wall wherein the chart includes horizontally extending and vertically extending lines, mounting a shoulder girdle harness onto the shoulder area of said person, wherein the shoulder girdle harness includes means for projecting a laser line beam and a laser dot beam onto the chart, mounting a pelvic girdle harness onto the pelvic area of said person, wherein said pelvic girdle includes means for projecting a laser line beam and a laser dot beam onto the chart, positioning the person in aligned and spaced relation to the chart and oriented to project the laser beams onto the chart to measure spinal tilt and torque, and reading the spinal tilt and torque values for the shoulder and pelvic areas.

* * * * *